United States Patent [19]

Andrisano et al.

[11] 4,168,375
[45] Sep. 18, 1979

[54] PROCESS FOR THE RECOVERY OF CEPHALOSPORIN C AND DERIVATIVES THEREOF

[75] Inventors: Renato Andrisano; Giuseppe Mascellani; Guido Guerra, all of Bologna, Italy

[73] Assignee: Alfa Farmaceutici, S.p.A., Bologna, Italy

[21] Appl. No.: 548,927

[22] Filed: Feb. 11, 1975

[30] Foreign Application Priority Data

Feb. 20, 1974 [GB] United Kingdom ............... 7699/74

[51] Int. Cl.$^2$ ................ C07D 501/08; C07D 501/12
[52] U.S. Cl. ........................................ 544/20; 544/19
[58] Field of Search ..................... 260/243 C; 544/20

[56] References Cited

U.S. PATENT DOCUMENTS

| | | | |
|---|---|---|---|
| 3,522,248 | 7/1970 | Voser | 260/243 C |
| 3,819,621 | 6/1974 | Morimoto et al. | 260/243 C |
| 3,821,208 | 6/1974 | Stables et al. | 260/243 C |
| 3,835,129 | 9/1974 | Wild | 260/243 C |
| 3,853,863 | 12/1974 | Jackson et al. | 260/243 C |

*Primary Examiner*—Donald G. Daus
*Assistant Examiner*—James H. Turnipseed
*Attorney, Agent, or Firm*—Stevens, Davis, Miller & Mosher

[57] ABSTRACT

A process for the recovery of cephalosporin C from an aqueous medium, including the steps of treating the medium with a sulphonyl chloride of formula R—SO$_2$Cl, in which R is a substituted or unsubstituted alkyl group having from 4 to 10 carbon atoms, or a substituted or unsubstituted aryl group, to convert the cephalosporin C to the corresponding sulphonamide and extracting the sulphonamide with an essentially water immiscible solvent. The sulphonyl chloride may be toluene-p-sulphonyl chloride, p-isopropylbenzenesulphonyl chloride or β-naphthalenesulphonyl chloride. The molar ratio of sulphonyl chloride to cephalosporin C present in the aqueous medium is from 3 to 10. The temperature of the reaction of sulphonyl chloride with cephalosporin C is maintained in the range from 10° to 20° C. The water immiscible solvent is selected from ethyl acetate, n-butanol and methylisobutylketone. The pH of the reaction medium is maintained at a value of from 7.5 to 9.5 by means of a buffering agent. The extraction of the sulphonamide of cephalosporin C is carried out at a pH of from 1 to 4.

12 Claims, No Drawings

PROCESS FOR THE RECOVERY OF CEPHALOSPORIN C AND DERIVATIVES THEREOF

The present invention relates to a process for the recovery of cephalosporin C from aqueous solutions, and particularly from fermentation broths, in the form of a derivative which is easily extractable with essentially water-immiscible solvents. The invention also relates to the preparation of 7-aminocephalosporanic acid from the derivatives so recovered.

Cephalosporin C, which has the formula:

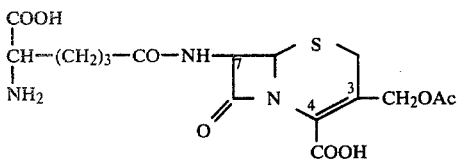
(I)

has acquired considerable importance in chemotherapy. Not only does it possess a certain, albeit limited, antibiotic activity itself, but also it is an important starting material for the preparation of 7-aminocephalosporanic acid (hereinafter referred to as 7-ACA), also known by the semi-systematic name 7β-amino-3-acetoxymethyl-ceph-3-em-4-carboxylic acid, and which has the formula:

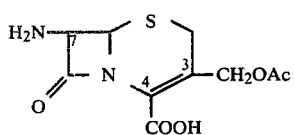
(II)

In both of the above formulae, the symbol Ac represents the acetyl group —CO.CH$_3$. 7-ACA is useful as an intermediate in the preparation of many semi-synthetic cephalosporins.

Cephalosporin C is prepared on an industrial scale by the fermentation of microorganisms of the genus Cephalosporium in an aqueous nutrient medium. At the end of the fermentation, cephalosporin C is present in the broth together with many other substances, of which some are nutrient substances originally present in the medium and others are fermentation products. The isolation of cephalosporin C from such fermentation broths has, therefore, for a long time, presented a very difficult problem. Methods widely used for this isolation involve expensive and complicated absorption and elution processes using resins, including ion exchange resins. These methods, however, have many disadvantages, including: great complexity of operation; large investment cost for resin columns; time-consuming operations, which may involve partial degradation of the cephalosporin C; requirement for large quantities of solvents, which are not always recoverable; and low absorption yields. A number of chemical methods for the isolation of cephalosporin C from fermentation broths has also been disclosed: these consist in treating the filtered broths with reactants capable of reacting with the amino group of cephalosporin C, the cephalosporin C derivatives thus obtained then being extracted with suitable solvents. However, the processes adopted to date have not been completely satisfactory in that both yields and purity of the derivatives isolated from the solvent are low. It is believed that this is due to the fact that many substances present in the fermentation broths contain amino groups capable of reacting with the reactant to produce derivatives which are extracted by the solvent together with the cephalosporin C derivatives.

We have now discovered a class of derivatives of cephalosporin C which may be isolated from fermentation broths and which are easily recoverable by extraction with an essentially water-immiscible solvent, whereas the recovery of similar derivatives of other amino group-containing substances present in the broths is substantially reduced. This class of derivatives has the further advantage that they may be used directly to produce 7-ACA without requiring intermediate conversion to cephalosporin C. These derivatives are the sulphonamides.

Thus, the present invention consists in a process for the recovery of cephalosporin C in the form of a sulphonamide from an aqueous medium, e.g. a fermentation broth, containing cephalosporin C, which process comprises: treating said medium with a sulphonyl chloride of formula R—SO$_2$Cl (in which R is a substituted or unsubstituted, preferably unsubstituted, alkyl group having from 4 to 10 carbon atoms, or a substituted or unsubstituted aryl, e.g. phenyl or naphthyl, group) to convert the cephalosporin C to the corresponding sulphonamide; and extracting the sulphonamide with an essentially water-immiscible solvent.

The substituents on Group R, particularly where R is a substituted aryl group are preferably one or more of: alkyl groups having from 1 to 6 carbon atoms, alkoxy groups having from 1 to 6 carbon atoms, halogen (e.g. chlorine, bromine, iodine) atoms and nitro groups.

The derivative recovered is believed to have the formula:

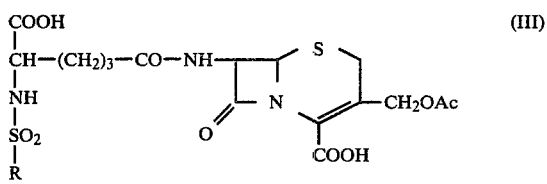
(III)

in which R is as above defined.

By "essentially water-immiscible solvent" we mean a solvent which is either immiscible with water or which, if partly miscible, is sufficiently immiscible to enable the solvent and the aqueous phase to be separated.

The aqueous medium containing the cephalosporin C may be the broth produced by fermentation, preferably after freeing the broth from the mycelium by filtration. If desired, the broth may, in addition to being freed from mycelium by filtration, also be freed from certain other impurities by treatment with acids and/or with solvents, for example acetone, according to known processes. It is also possible to use purified fermentation broths which have been concentrated by conventional techniques e.g. by vacuum concentration or by resin absorption and subsequent elution.

The process of the present invention has many advantages over similar known processes for the recovery of cephalosporin C from fermentation broths using different derivatives. One of the main advantages is that the process of the present invention gives good results even if the concentration of cephalosporin C in the fermentation broth is low. This unique feature makes the process of the present invention widely applicable on an industrial scale.

Examples of sulphonyl chlorides which may be used in the present invention are: toluene-p-sulphonyl chloride; dimethylbenzenesulphonyl chloride; p-isopropylbenzenesulphonyl chloride; butylbenzenesulphonyl chloride; β-naphthalenesulphonyl chloride; and p-nitrobenzenesulphonyl chloride. These sulphonyl chlorides produce, respectively, the following sulphonamides of celphalosporin C: toluene-p-sulphonamide of cephalosporin C; dimethylbenzenesulphonamide of cephalosporin C; p-isopropylbenzenesulphonamide of cephalosporin C; butylbenzenesulphonamide of cephalosporin C; β-naphthalenesulphonamide of cephalosporin C; and p-nitrobenzenesulphonamide of cephalosporin C. Of these, the p-isopropylbenzenesulphonamide of cephalosporin C and the β-naphthalenesulphonamide of cephalosporin C are new compounds, which compounds also form part of the present invention.

To allow complete removal of the cephalosporin C from the aqueous medium, the minimum quantity of sulphonyl chloride employed should be 1 mol per mol of cephalosporin C in the aqueous medium; however, we prefer to use more than 1 mol of sulphonyl chloride per mol of cephalosporin C and particularly prefer to use from 3 to 10 mols per mol of cephalosporin C. The process may be carried out at any convenient temperature, although normally at a temperature of from 0° to 40° C. The temperature chosen should be so selected as to achieve a satisfactory rate of reaction while avoiding degradation of cephalosporin C and its derivatives. We, therefore, prefer to carry out the process of the invention at a temperature of from 10° to 20° C.

The reaction of the sulphonyl chloride with cephalosporin C produces hydrogen chloride as a by-product and this is preferably removed during the reaction. Removal of this hydrogen chloride is best achieved by carrying out the reaction in the presence of a material capable of binding the acid. It is particularly preferred that the pH of the reaction medium during the reaction should be maintained at a value above 7, and preferably in the range of from 7.5 to 9.5, by means of one or more basic compounds, such as alkali metal hydroxides, carbonates or bicarbonates, or organic bases. More preferably, the pH of the reaction medium is maintained at the indicated value by means of a buffering agent, such as borax. After reacting the cephalosporin C with the sulphonyl chloride, the aqueous reaction medium is then extracted using a solvent which is immiscible or essentially immiscible with water and in which the sulphonamide of cephalosporin C is soluble. The extraction of the sulphonamide of cephalosporin C is preferably carried out at a pH below 7, more preferably at a pH of from 1 to 4.

Examples of suitable solvents for use in the extraction are: the lower alkyl esters of lower aliphatic acids, such as ethyl acetate, propyl acetate, and butyl acetate; alcohols having at least 4 carbon atoms, such as n-butanol; the di(lower alkyl) ketones, such as methyl isobutyl ketone; cyclohexanone; and halogenated hydrocarbons, such as methylene chloride and chloroform. By "lower alkyl" we mean an alkyl group having from 1 to 5 carbon atoms and "lower aliphatic" is to be construed correspondingly. The lower aliphatic acid preferably contains 2 or 3 carbon atoms.

The sulphonamide derivative of cephalosporin C may be recovered from the organic extract by evaporation of the organic solvent, preferably under reduced pressure. The sulphonamide derivative may then be converted into a poorly soluble salt, e.g. to an alkali metal salt or to a salt of an organic base. Conversion to an alkali metal salt, for example, the sodium salt, may be achieved by dissolving the residue after evaporation in a solvent such as n-butanol, to which is gradually added a solution of sodium 2-ethylhexanoate in n-butanol to a final pH of from 5 to 6. The mixture is then cooled to 0°–5° C. for a few hours, after which the solid sodium salt of the sulphonamide of cephalosporin C is filtered off, washed and dried at low temperature under reduced pressure. Alternatively, a salt of an organic base may be prepared by the addition of a compound such as: quinoline; cyclohexylamine; 5-ethyl-2-methylpyridine; 2-picoline; 3-picoline; 4-picoline; N-ethylmorpholine, N-methylmorpholine, 2,6-lutidine; N,N-diethylcyclohexylamine; hexamethylenetetramine, N,N-diethylbenzylamine; or N,N-dibenzylethylenediamine.

The sulphonamide derivatives of cephalosporin C, either in the form of a free acid or in the form of a salt, may be used directly for the preparation of 7-ACA. This process may be carried out using known techniques and will, in general, comprise the following steps:

(a) protecting the carboxylic acid group by forming an ester;

(b) halogenating the ester to give the corresponding imino-halide;

(c) reacting the imino-halide with a lower aliphatic alcohol to give the corresponding imino-ether; and (d) hydrolyzing the imino-ether under acidic conditions to give 7-ACA.

According to the present invention, higher yields in 7-ACA referred to the cephalosporin C are obtained, if the starting sulphonamide derivatives of cephalosporin C are purified before conversion to 7-ACA with the aid of ion exchange resins.

Although the invention has been described with reference to the isolation of cephalosporin C itself, it will be appreciated that the invention is equally applicable to the isolation of other cephalosporin C derivatives having different substituents at the 3 and 4 positions, i.e., in which the $CH_2OAc$ group at the 3-position has been replaced by another group (generally a substituted or unsubstituted acyloxymethyl or alkoxymethyl group) and/or in which the carboxylic acid group at the 4-position has been replaced by another group, generally an ester group, or in which the 3- and 4-positions are joined through a lactone oxygen atom. The necessity to isolate such further derivatives may arise if chemical conversions are carried out on the cephalosporin C prior to its complete isolation from the fermentation broth.

The invention is further illustrated with reference to the following examples.

EXAMPLE 1

2,000 ml of acetone were added to 2,000 ml of an aqueous solution containing 14.45 g of cephalosporin C sodium dihydrate, and the pH was raised to 8.5 by the addition of 30% aqueous sodium hydroxide. Over 30 minutes, 17.4 g of toluene-p-sulphonyl chloride dissolved in 100 ml of acetone were added with stirring, while maintaining the pH at 8.5 with 30% aqueous sodium hydroxide. The agitation was maintained for a further hour. The pH was then adjusted to 7 and the acetone was evaporated under vacuum at 30° C.

1,000 ml of methyl isobutyl ketone (MIBK) were added and the pH was lowered to 2.0 by the addition of concentrated hydrochloric acid, with stirring. Sodium chloride was added and the organic layer was separated. The aqueous layer was then extracted with three portions, each of 600 ml, of MIBK. The extracts were combined and dried over anhydrous sodium sulphate, and the solvent was then evaporated under vacuum at 30° C. To the residual oil dissolved in 150 ml of n-butanol were added 24 ml of a 2.6 molar solution of sodium 2-ethylhexanoate in n-butanol, to a final pH of 5.5. After allowing the mixture to rest overnight at low temperature, the precipitate which formed was filtered off, washed with ether and dried under vacuum.

15.8 g of the sodium salt of toluene-p-sulphonamide of cephalosporin C, having a titre of 87.1%, were obtained. This corresponds to a yield of 73.5%.

EXAMPLE 2

A fermentation broth containing cephalosporin C was acidified, filtered, mixed with an equal volume of acetone, and filtered again. 2,000 ml of the resulting solution, which had a cephalosporin C content (expressed as the sodium salt dihydrate) of 1,730 mcg/ml, were raised to a pH of 8.8±0.2 by addition of 20% aqueous sodium hydroxide. A solution of 8.3 g of toluene-p-sulphonyl chloride in 50 ml of acetone was then added with stirring over 5 minutes. The stirring was continued for a further 90 minutes, while the pH was maintained at the same value with 20% aqueous sodium hydroxide. The pH was then adjusted to 7.0 and the acetone was evaporated under vacuum at 30° C. 300 ml of MIBK were added and the pH was lowered to 2.0 by the addition of 5N hydrochloric acid. The organic phase was separated and the aqueous phase was extracted with five 100 ml portions of MIBK. The organic extracts were combined, dried over anhydrous sodium sulphate and concentrated under vacuum at 35° C. The residual oil was then dissolved in 70 ml of n-butanol and the pH value adjusted to 6.5 with 15 ml of a 1.84 molar solution of sodium 2-ethylhexanoate in n-butanol. After allowing the mixture to rest overnight at a low temperature, the precipitate which formed was filtered, washed with ether and dried under vacuum, yielding 7.94 g of the sodium salt of toluene-p-sulphonamide of cephalosporin C, having a spectrophotometric titre of 42%. The yield was 73%.

The same process above described, with the only difference that the pH of the reaction mixture was maintained at about 9 with the aid of $Na_2B_4O_7.10H_2O$ instead of NaOH, gave a yield of 89% of sodium salt of cephalosporin C-toluene-p-sulphonamide having a spectrophotometric titre of 45%.

EXAMPLE 3

A fermentation broth containing cephalosporin C was acidified, filtered, mixed with an equal volume of acetone, and again filtered. 1,000 ml of the resulting solution, which had a cephalosporin C content (expressed as the sodium salt dihydrate) of 1,780 mcg/ml, were adjusted to pH 7 by the addition of 20% aqueous sodium hydroxide. 4.8 g of sodium bicarbonate were added to the resulting solution, after which 2.9 g of toluene-p-sulphonyl chloride dissolved in acetone were added over 5 minutes. After 1 hour, a further 1.45 g of toluene-p-sulphonyl chloride were added and a further 1.45 g were added after 2 hours. The pH was kept constant at 8.5. After three hours, the pH was lowered to 7.0 by addition of hydrochloric acid and the acetone was evaporated under vacuum at 30° C. 200 ml of MIBK were added and the pH was adjusted to 2.0, while stirring. The organic phase was separated and the aqueous phase was extracted with three 100 ml portions of MIBK. The organic extracts were combined and washed with 100 ml of cool water; the washing water was extracted with 50 ml of MIBK. All organic extracts were combined and dried over anhydrous sodium sulphate, and the solvent was then evaporated under vacuum at 35° C.

To the residual oil, dissolved in 40 ml of n-butanol, were added 6.6 ml of a 1.86 molar solution of sodium 2-ethylhexanoate in n-butanol, adjusting the pH to 5.6. After resting overnight at low temperature, the resulting precipitate was filtered, washed with ether and dried under vacuum, yielding 3.73 g of the sodium salt of toluene-p-sulphonamide of cephalosporin C, having a titre of 40.3%. The yield was 65.2%.

EXAMPLE 4

1,000 ml of a filtered fermentation broth were concentrated under vacuum at 35° C. to a volume of 280 ml. The cephalosporin C content (expressed as the sodium salt dihydrate) was 10,910 mcg/ml. 280 ml of acetone were added, the precipitate was filtered off, washed with 40 ml of a 1:1 mixture of acetone and water and discarded. The washings were combined with the filtered solution. The pH was then raised to 8.8±0.2 by addition of 30% sodium hydroxide and 7.2 g of toluene-p-sulphonyl chloride dissolved in 50 ml of acetone were added over three hours, while maintaining the pH between 8.5 and 9 with addition of 30% sodium hydroxide and stirring. Stirring was maintained for a further hour while maintaining the pH at the same value by addition of 30% sodium hydroxide. The pH was then lowered to 7.0 by addition of concentrated hydrochloric acid and the acetone was evaporated under vacuum at 30° C. 100 ml MIBK were added and the pH was lowered to 2.0 by addition of concentrated hydrochloric acid, with stirring.

The organic phase was separated and the aqueous phase was extracted four times with 50 ml portions of MIBK. The organic extracts were combined and dried. The solvent was then evaporated under vacuum and the residual oil was dissovled in 80 ml of n-butanol, after which a solution of sodium 2-ethylhexanoate in n-butanol was added to a pH of 6.5. The precipitate which formed was recovered and dried, yielding 6.24 g (73%) of the sodium salt of toluene-p-sulphonamide of cephalosporin C having a spectrophotometric titre of 45.2%.

EXAMPLE 5

1,000 ml of a filtered fermentation broth having a cephalosporin C content (expressed as the sodium salt dihydrate) of 3,300 mcg/ml were mixed with 1,000 ml of acetone and the precipitate filtered off. The pH of the mixture was adjusted to 8.8±0.2 and maintained at this value by addition of 30% aqueous sodium hydroxide while a solution of 7.2 g of toluene-p-sulphonyl chloride in 50 ml of acetone were added over three hours, after which the solution was stirred for a further hour. The pH was then lowered to 7.0 by addition of concentrated hydrochloric acid and the acetone was evaporated under vacuum. The solution was then extracted at pH 2 with one portion of 200 ml and four portions each of 100 ml of MIBK. The organic extracts were washed with four portions each of 50 ml of cool water and the aqueous washings were extracted with 50 ml of MIBK.

The combined organic extracts were concentrated under vacuum to 100 ml, and 3.5 ml of quinoline were added. After resting overnight at low temperature, the resulting precipitate was filtered off, washed with ether and dried, yielding 3.8 g of the quinoline salt of toluene-p-sulphonamide of cephalosporin C having a spectrophotometric titre of 68.5%. The yield was 53.5%.

EXAMPLE 6

A fermentation broth containing cephalosporin C was acidified, filtered, mixed with an equal volume of acetone, and filtered again. 3,000 ml of the filtrate, having a cephalosporin C content (expressed as the sodium salt dihydrate) of 1,750 mcg/ml, were adjusted to pH 9.0 by addition of 30% sodium hydroxide, with stirring, and then 12.6 g of toluene-p-sulphonyl chloride in 50 ml of acetone were added over 5 minutes while maintaining the pH at 9. The solution was agitated for 90 minutes at pH 9.

The pH was then lowered to 7.0 and the acetone was evaporated under vacuum at 30° C. After extracting the solution at pH 2 with one 700 ml portion and with four 200 ml portions of MIBK, the organic extracts were combined and washed with 300 ml of water. The aqueous washings were extracted with 150 ml of MIBK, which was then added to the other organic extracts. The combined organic extracts were dried over anhydrous sodium sulphate and then divided into three equal portions, which were treated as follows:

(A) The solvent was evaporated from this portion and the residue was dissolved in 50 ml of n-butanol. 8 ml of a 1.84 molar solution of sodium 2-ethylhexanoate in n-butanol were then added to a final pH of 5.6, yielding 3.95 g of the sodium salt of toluene-p-sulphonamide of cephalosporin C having a titre of 43.2%. The yield was 75%.

(B) 6.6 ml of the above described solution of sodium 2-ethylhexanoate were added to this portion, to a final pH of 5.6. The resulting suspension was then concentrated under vacuum at 35° C. to a volume of 100 ml and, after cooling, the precipitate was filtered and dried, yielding 3.85 g of the sodium salt of toluene-p-sulphonamide of cephalosporin C having a titre of 44.2%. The yield was 75%.

(C) The solvent was evaporated from this portion and the residue was dissolved in 40 ml of n-butanol, after which 2.45 ml of N-methylmorpholine were added. The resulting tarry solid was separated, crushed in ether and dried under vacuum, yielding 2.6 g of the N-methylmorpholine salt of toluene-p-sulphonamide cephalosporin C, having a titre of 55%. The yield was 57.5%.

EXAMPLE 7

To 600 ml of a purified and concentrated broth containing 15,490 mcg/ml of cephalosporin C (expressed as the sodium salt dihydrate) were added 500 ml of acetone. The pH of the resulting mixture was adjusted to a value of 8 by addition of 30% aqueous sodium hydroxide at 10° C., after which 15 g of toluene-p-sulphonyl chloride dissolved in 100 ml of acetone were added over 3 hours, while maintaining the pH at a value of 8 by addition of 30% sodium hydroxide. After agitation for 90 minutes, the acetone was evaporated and the solution was extracted with one 200 ml portion and two 100 ml portions of MIBK. The combined extracts were washed twice with a saturated solution of sodium chloride and the solvent was then evaporated off. The residue was dissolved in n-butanol and treated with a 3 molar solution of sodium 2-ethylhexanoate in n-butanol to a final pH of 5.5.

The resulting precipitate was filtered, washed with ether and dried, giving 9.5 g (yield 78.5%) of the sodium salt of toluene-p-sulphonamide of cephalosporin C having a titre of 85.1%.

Melting point 149°–153° C.

Flex point of UV absorption at 262 nm.

I.R. peaks at 3440, 2960, 1765, 1655, 1610, 1528, 1398, 1230, 1158, 1090, 1025, 812 and 658 cm$^{-1}$.

By thin layer chromatography using as a mobile phase a mixture of isopropanol/methanol/buffer at pH 5.8 (125:25:6.5), a spot is obtained at Rf 0.7 detectable as a white spot at warm with $J_2/NaN_3$.

EXAMPLE 8

1,000 ml of an aqueous solution containing 4,800 mcg/ml of cephalosporin C (expressed as the sodium salt dihydrate) were mixed with 1,000 ml of acetone, the pH was adjusted to 8.5–9 by the addition of 30% aqueous sodium hydroxide and, maintaining the pH at this value, a solution of 6.7 g of p-isopropylbenzenesulphonyl chloride in 50 ml of acetone was added. The mixture was stirred for a further 90 minutes at the same pH, after which the pH was lowered to a value of 7 and the acetone was evaporated under vacuum at 30° C. The pH was then reduced further to a value of 2 and the solution was extracted with one 400 ml portion and three 100 ml portions of MIBK. The combined organic extracts were dried and the solvents evaporated off. The residue was then dissolved in 80 ml of n-butanol and brought to a pH of 6.5 by the addition of a 1.84 molar solution of sodium 2-ethylhexanoate in n-butanol. The precipitate which formed was filtered, washed with ether and dried, yielding 6.4 g (75%) of the sodium salt of p-isopropylbenzenesulphonamide of cephalosporin C, having a titre of 75.9%.

I.R. peaks at 3430, 3380, 3050, 2960, 1755, 1655, 1600, 1540, 1400, 1230, 1160, 1090, 1030, 830, 750, 690, 650 cm$^{-1}$.

EXAMPLE 9

A fermentation broth containing cephalosporin C was acidified, filtered, mixed with an equal volume of acetone and again filtered. 1,350 ml of the filtrate containing 1,730 mcg/ml of the sodium salt of cephalosporin C (expressed as the sodium salt dihydrate) were then adjusted to a pH of 8.8±0.2 by addition of 20% sodium hydroxide. 6.5 g of p-isopropylbenzenesulphonyl chloride in 50 ml of acetone were then added with stirring over 5 minutes. The stirring was maintained for 1 hour at the same pH, after which the acetone was evaporated under vacuum and the residue was extracted at pH 2 with one 150 ml portion and subsequently with five 75 ml portions of MIBK. The organic extracts were combined, dried over anhydrous sodium sulphate and evaporated under vacuum. The residual oil was then dissolved in 50 ml of n-butanol and a 1.84 molar solution of sodium 2-ethylhexanoate in n-butanol was added, bringing the pH to 6.5. After allowing the mixture to rest overnight at a low temperature, the precipitate which had formed was filtered, washed with ether and dried under vacuum, giving 6.4 g (a yield of 81%) of the sodium salt of p-isopropylbenzenesulphonamide of cephalosporin C, having a titre of 40.5%.

EXAMPLE 10

After acidifying and filtering a fermentation broth, 355 ml of the filtrate were mixed with 670 ml of acetone and again filtered. To the solution, which contained 1 g of sodium salt of cephalosporin C (as the dihydrate), were added with stirring over 5 minutes a solution of 3.85 g of 2-naphthalenesulphonyl chloride in 50 ml of acetone, while maintaining the pH at 9.0 with 30% aqueous sodium hydroxide. Stirring was continued for a further 2 hours at the same pH, after which the pH was lowered to 7.5 and the acetone was evaporated under vacuum. The pH of the residue was further reduced to 2 and the residue was then extracted with one 200 ml portion and with three 100 ml portions of MIBK. The organic extracts were combined and washed with 100 ml of water and the aqueous washings were extracted with 50 ml of MIBK. All of the combined organic extracts were dried and the solvent was evaporated under vacuum. The oily residue was dissolved in 40 ml of n-butanol and 6 ml of a 2 molar solution of sodium 2-ethylhexanoate in n-butanol was added, giving a final pH of 5.5. The mixture was allowed to rest at a low temperature overnight, forming a precipitate, which was filtered, washed with ether and dried to give 4.1 g of the 2-naphthalenebenzenesulphonamide of cephalosporin C.

I.R. peaks at 3450, 3060, 2925, 1770, 1730, 1660, 1530, 1385, 1230, 1160, 1075, 1035, 820, 750, 660 cm$^{-1}$.

EXAMPLE 11

3.07 g of the sodium salt of toluene-p-sulphonamide of cephalosporin C having a titre of 83.8% were suspended in 30 ml of methylene chloride. 1.4 ml of triethylamine and 1.9 ml of N,N-dimethylaniline were then added and then 2.4 ml of dimethyldichlorosilane were added over 5 minutes with stirring. Stirring was maintained for 1 hour at 28° C. The solution was then cooled to a temperature of −60° C., after which a solution of 3.13 g of PCl$_5$ in 30 ml of methylene chloride was slowly added, followed by 2.5 ml of N,N-dimethylaniline. After 2 hours of agitation at −40° C. the temperature was reduced again to −60° C. and 0.34 of N,N-dimethylaniline in 9 ml of methanol were added. After two hours at −40° C., 10 ml of water at 90° C. were added and agitation was continued for 5 minutes at 4° C. The aqueous phase was then recovered and the organic phase was extracted with 10 ml of cool water. The combined aqueous extracts were washed with 10 ml of methylene chloride and the pH was adjusted to 3.6–3.7 by addition of concentrated aqueous ammonia solution, with stirring. After allowing the mixture to rest overnight at a low temperature, the precipitate which formed was filtered, washed with methylene chloride, water, acetone and ether, to give 0.80 g (65%) of 7-aminocephalosporanic acid with a spectrophotometric titre of 94.4%.

EXAMPLE 12

Following the procedure described in Example 11, but using the sodium salt of toluene-p-sulphonamide of cephalosporin C having a titre of 38.8%, 7-ACA having a titre of 90.7% was obtained in 55.1% yield.

EXAMPLE 13

Following the procedure described in Example 11, from the sodium salt of p-isopropylbenzenesulphonamide of cephalosporin C having a titre of 76%, 7-ACA having a titre of 94.1% was obtained in 68% yield.

EXAMPLE 14

Following the procedure described in Example 11, 7-ACA having a titre of 91.4% was obtained in 41.4% yield from the sodium salt of p-isopropylbenzenesulphonamide of cephalosporin C having a titre of 43.8%.

What is claimed is:

1. A process for the recovery of cephalosporin C from an aqueous medium, wherein said medium is treated with a sulphonyl chloride of the formula R—SO$_2$Cl, in which R is a radical selected from the group consisting of p-tolyl, dimethyl phenyl, p-isopropyl phenyl, butyl phenyl, β-naphthyl, and p-nitrophenyl, to convert the cephalosporin C to the corresponding sulphonamide and the sulphonamide is extracted with an essentially water immiscible solvent, the molar ratio of sulphonyl chloride to cephalosporin C being higher than 1 and the temperature of the reaction of sulphonyl chloride with cephalosporin C being in the range of from 0° to 40° C.

2. The process according to claim 1 wherein the aqueous medium is a fermentation broth containing cephalosporin C.

3. The process according to claim 1 wherein the sulphonyl chloride is toluene-p-sulphonyl chloride.

4. The process according to claim 1 wherein the sulphonyl chloride is p-isopropylbenzenesulphonyl chloride.

5. The process according to claim 1 wherein the sulphonyl chloride is β-naphthalenesulphonyl chloride.

6. The process according to claim 1 wherein the molar ratio of sulphonyl chloride to cephalosporin C present in the aqueous medium is from 3 to 10.

7. The process according to claim 1 wherein said temperature is from 10° to 20° C.

8. The process according to claim 1 wherein said water immiscible solvent is selected from the group consisting of ethyl acetate, n-butanol and methylisobutylketone.

9. The process according to claim 1 including maintaining the pH of the reaction medium at a value above 7 by means of borax.

10. The process according to claim 9 wherein said pH is in a range of from 7.5 to 9.5.

11. The process according to claim 1 wherein said extraction of the sulphonamide of cephalosporin C is carried out at a pH below 7.

12. The process according to claim 11 wherein said pH is from 1 to 4.

* * * * *